United States Patent [19]

Meek et al.

[11] Plant 4,897

[45] Oct. 19, 1982

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 160,824

[22] Filed: Jun. 18, 1980

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar known by the cultivar name Aristocrat and characterized as to uniqueness by the combined characteristics of flat capitulum form; daisy capitulum type; dark yellow ray floret color, with minimum color oxidation; diameter across face of capitulum ranging from 85 to 95 mm. at maturity; uniform eight week photoperiodic flowering response to short days; long peduncle length; medium plant height (cut spray culture); and semi-upright branching pattern.

3 Drawing Figures

The present invention comprises a new and distinct cultivar of *Chrysanthemum morifolium,* Ramat., hereinafter referred to by the cultivar name Aristocrat.

Aristocrat is a product of a planned breeding program which had the objective of creating new chrysanthemum cultivars with daisy capitulum type, yellow ray floret color, eight or nine week flowering response, and with the ability to produce commercially acceptable quality in year round cut mum programs. Such traits in combination were not present in previously available commercial cultivars.

Aristocrat was originated from a hybridization made in a controlled breeding program in Salinas, Calif. in 1977. The female parent was Florida Marble, disclosed in U.S. Plant Pat. No. 3,288. The male parent of Aristocrat was Celebration, disclosed in U.S. Plant Pat. No. 3,778. Aristocrat was discovered and selected as one flowering plant within the progeny of the stated parentage by William E. Duffett on May 23, 1978 in a controlled environment in Salinas, Calif.

The first act of asexual reproduction of Aristocrat was accomplished when vegetative cuttings were taken from the initial selection in July, 1978 in a controlled environment in Salinas, Calif. by a technician working under formulations established and supervised by Jack M. Meek. Horticultural examination of selected units initiated Nov. 24, 1978 has demonstrated that the combination of characteristics as herein disclosed for Aristocrat are firmly fixed and are retained through successive generations of asexual reproduction.

Aristocrat has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Aristocrat which in combination distinguish this chrysanthemum as a new and distinct cultivar:

(1) flat capitulum form;

(2) daisy capitulum type;

(3) dark yellow ray floret color with minimum color oxidation;

(4) yellow-green (immature) to yellow (mature) disc floret color;

(5) diameter across face of capitulum ranging from 85 to 95 mm. at maturity;

(6) uniform eight week photoperiodic flowering response to short days;

(7) long peduncle length, ranging from 195 to 260 mm., (8) medium plant height (requiring one to two long day weeks prior to short days to attain a flowered plant height of 65 to 75 cm. for May through October flowerings); and (9) semi-upright branching pattern.

Of the many commercial cultivars known to the present inventors, the most similar in comparison to Aristocrat is Florida Marble. Reference is made to attached Chart A which compares certain characteristics of Aristocrat to those same characteristics of Florida Marble. In general comparison to Florida Marble, Aristocrat has darker yellow ray floret color, longer color retention, large diameter across face of capitulum, and shorter flowering response period. The capitulum form, capitulum type, plant height, and peduncle length of Aristocrat are similar to those same characteristics of Florida Marble.

The accompanying photographic drawings show typical inflorescence and foliage characteristics of Aristocrat with colors being as nearly true as possible with illustrations of this type. Sheet 1 is a color photograph of Aristocrat. Sheet 2 is a black and white photograph showing three views of the inflorescence of Aristocrat. Sheet 3 is a black and white photograph showing the foliage of Aristocrat at three stages of growth.

In the following description, color references are made to The Royal Horticultural Society (R.H.S.) Color Chart. The color values were determined between 1:30 and 2:00 P.M. on May 10, 1979 under 100 foot-candle light intensity at Salinas, Calif.

Classification:

*Botanical.*—*Chrysanthemum morifolium,* Ramat., cv Aristocrat.

*Commercial.*—Cut daisy spray chrysanthemum.

I. Inflorescence:

A. *Capitulum.*—Form: flat. Type: daisy. Diameter across face: 85 to 95 mm.

B. *Corolla of ray florets.*—General tonality (from a distance of three meters): dark yellow, 6-A to 6-C. Color (abaxial): 6-A but more intense to 5-B. Color (adaxial): 6-A oxidizing to 5-B.

C. *Corolla of disc florets.*—Color (abaxial): 12-A. Color (adaxial): 143-C (immature) to 12-A (mature).

D. *Reproductive organs.*—Androecium: present disc florets only; scant to numerous; scant pollen. Gynoecium: present both ray and disc florets.

II. Plant:

A. *General appearance.*—Branching pattern: semi-upright. Height: medium, 60 to 70 cm. given no long days for May through October flowerings.

B. *Foliage.*—Color (abaxial): approximately 137-A. Color (adaxial): approximately 137-C overlaid with white. Shape: moderately lobed and slightly serrated.

CHART A

COMPARISON OF ARISTOCRAT AND FLORIDA MARBLE

| CULTIVAR | RAY FLORET COLOR | CAPITULUM FORM AND TYPE | PLANT HEIGHT |
|---|---|---|---|
| ARISTOCRAT | Dark yellow with minimum color oxidation | Flat Daisy | Medium |

CHART A-continued

COMPARISON OF ARISTOCRAT AND FLORIDA MARBLE

| | | | |
|---|---|---|---|
| FLORIDA MARBLE | Medium yellow oxidizing to light yellow | Flat Daisy | Medium |

| CULTIVAR | DIAMETER ACROSS FACE OF CAPITULUM | FLOWERING RESPONSE PERIOD | PEDUNCLE LENGTH |
|---|---|---|---|
| ARISTOCRAT | 85 to 95 mm. | 8 week | Long, 195 to 260 mm. |
| FLORIDA MARBLE | 70 to 85 mm. | 9 week | Long, 180 to 250 mm. |

COMPARISONS MADE OF PLANTS GROWN AS SINGLE STEM CUT SPRAYS IN SALINAS, CALIFORNIA

We claim:

1. A new and distinct cultivar of *Chrysanthemum morifolium,* Ramat., plant known by the cultivar name Aristocrat and particularly characterized as to uniqueness, as herein described and illustrated, by the combined characteristics of flat capitulum form; daisy capitulum type; dark yellow ray floret color, with minimum color oxidation; diameter across face of capitulum ranging from 85 to 95 mm. at maturity; uniform eight week photoperiodic flowering response to short days; long peduncle length; medium plant height when grown as a single stem cut spray; and semi-upright branching pattern.

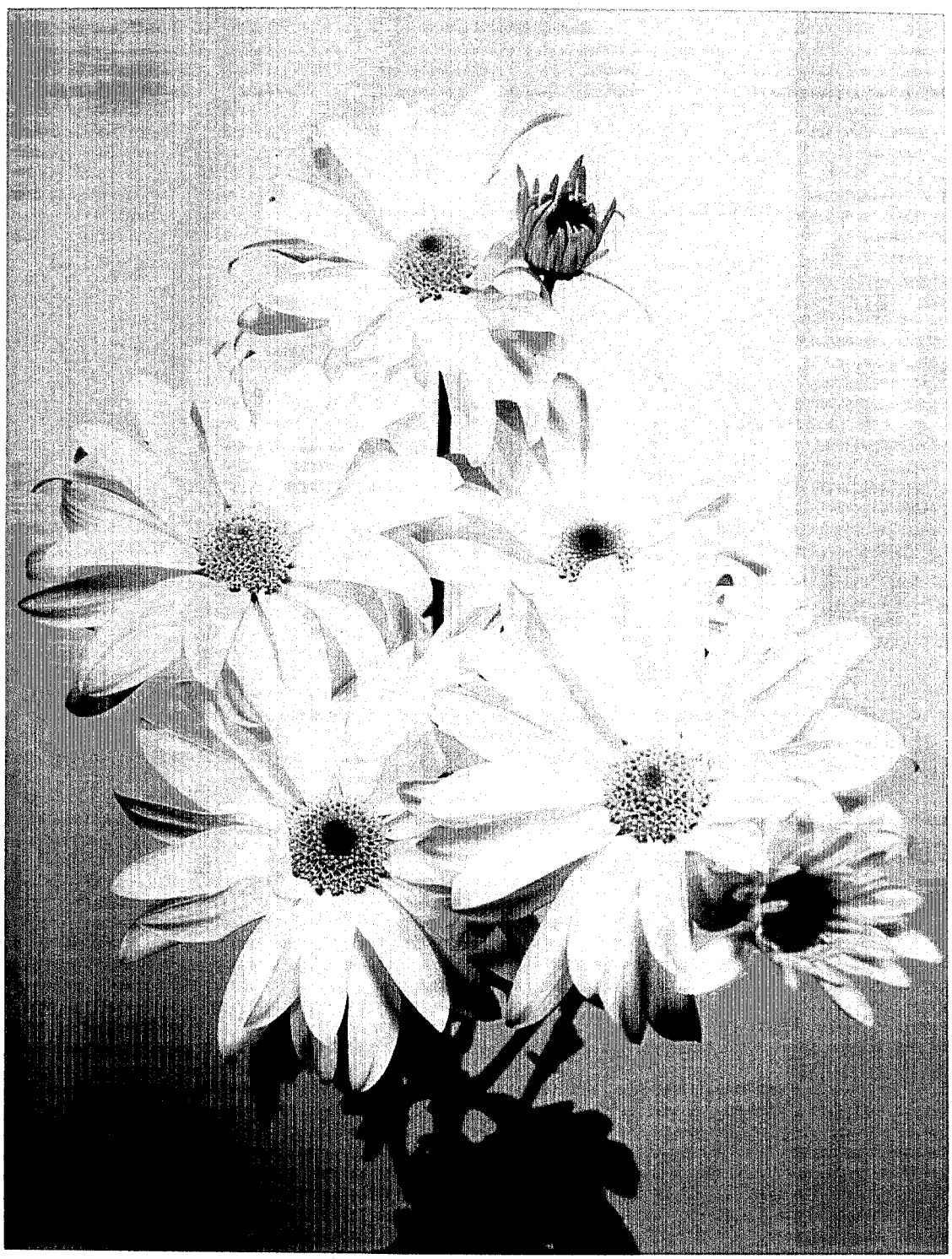

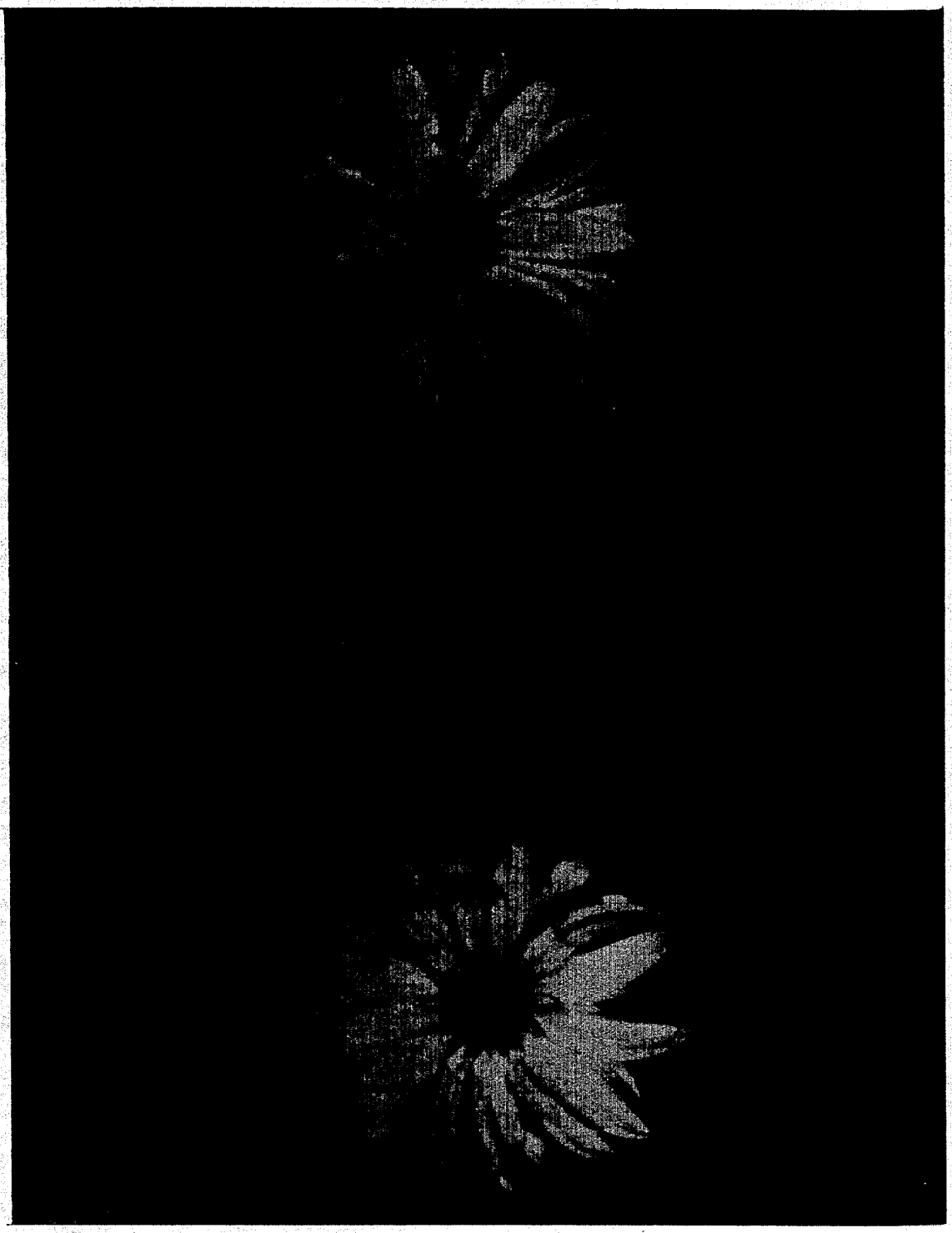

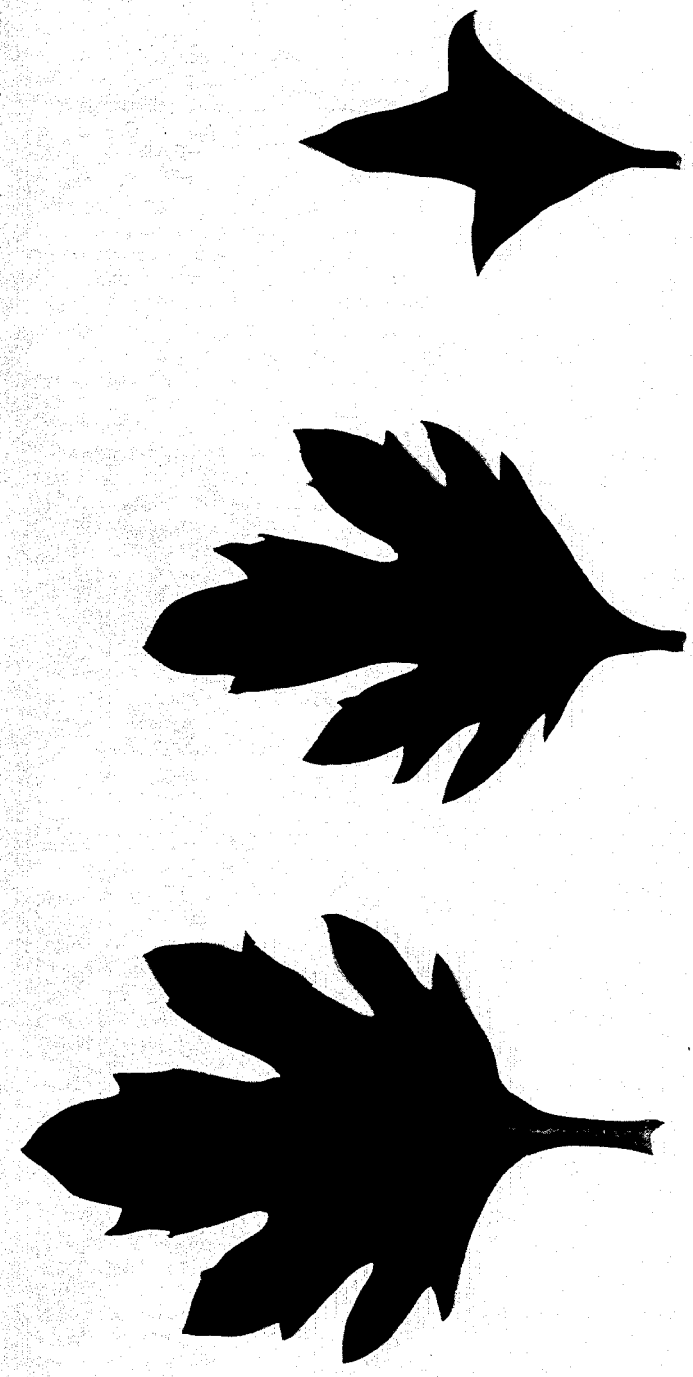

* * * * *